United States Patent [19]

Brass et al.

[11] Patent Number: 5,260,598
[45] Date of Patent: Nov. 9, 1993

[54] DEVICE FOR SEPARATION OF MEDIA INTO THEIR COMPONENTS HAVING MEANS FOR DETECTION AND ADJUSTMENT OF THE PHASE BOUNDARY

[75] Inventors: Henning Brass, Bad Homburg; Stefan Kreber, Saarbrucken; Arthur Meisberger, St. Wendel-Winterbach, all of Fed. Rep. of Germany

[73] Assignee: Fresenius AG, Bad Homburg, Fed. Rep. of Germany

[21] Appl. No.: 952,940

[22] Filed: Sep. 29, 1992

[30] Foreign Application Priority Data

Oct. 4, 1991 [DE] Fed. Rep. of Germany ....... 4132965

[51] Int. Cl.$^5$ .............................................. G01N 15/06
[52] U.S. Cl. ...................................... 250/574; 356/427
[58] Field of Search .................. 250/574, 576, 336.1, 250/226; 356/427, 23, 426; 210/789, 516, 781, 782; 494/16, 38, 37

[56] References Cited

U.S. PATENT DOCUMENTS

| | | | |
|---|---|---|---|
| 4,154,690 | 5/1979 | Ballies | 210/789 |
| 4,740,077 | 4/1988 | Goodwill | 356/427 |
| 4,814,282 | 3/1989 | Holen et al. | 250/576 |

FOREIGN PATENT DOCUMENTS

3301113 7/1983 Fed. Rep. of Germany .
3413065 10/1984 Fed. Rep. of Germany .

Primary Examiner—David C. Nelms
Assistant Examiner—Que T. Le
Attorney, Agent, or Firm—Robbins, Berliner & Carson

[57] ABSTRACT

A separation device with a transparent separation chamber, whereby a direct light source illuminates the components to be separated and the individual components reflect the light intensity as a function of their individual coloring (brightness) via optics onto a linear group of photodetectors. The signals received by the detectors are forwarded to a computing unit in which they are processed. A regulating unit, which operates very precisely due to the accuracy and the high speed of the receiver and computing unit, is controlled according to a program and thus assures optimum separation performance of the separation device.

15 Claims, 3 Drawing Sheets

DEVICE FOR SEPARATION OF MEDIA INTO THEIR COMPONENTS HAVING MEANS FOR DETECTION AND ADJUSTMENT OF THE PHASE BOUNDARY

BACKGROUND OF THE INVENTION

The invention concerns a device for separation of media into their components through density centrifugation in a separation chamber, with an arrangement for detection and adjustment of the phase boundary between at least two optically differentiable fractions of the medium (phase detector), consisting of a light source, which illuminates the separation chamber in the region of the self-adjusting phase boundaries, of a light receiving arrangement, and optics, which reproduce a specific section of the region on the light receiving arrangement, which responds to different light signals according to optical differences between the fractions, and of a control circuit, connected downstream from the light receiving arrangement, to trigger control signals.

Such a device is known, for example, from U.S. Pat. No. 4,724,317 and from DE-A 33 01 113 (=EP-B 0 116 716). The media in question are primarily body fluids, in particular, blood.

The arrangement for detection and adjustment of the phase boundary in such devices, the phase detector, is supposed to improve the separation performance of the separation device. For this, the known arrangement uses the different light permeability of the individual fractions of the medium. For this purpose, the light source and the light receiving arrangement are disposed with the optics such that the optics are impacted by the light which passes through the fractions and is weakened differently by the differing absorption in the individual fractions. Based on the relationship of the light signals, the phase boundary is specified or other procedures are triggered.

In such an arrangement it is disadvantageous that the specification of the phase boundary or the generation of other control signals takes place solely on the basis of a light-dark differentiation, such that it is possible neither to differentiate between the individual fractions which are impermeable to light nor to use a separation device equipped with such a phase detector with blood plasma which is highly turbid due to the donor's condition.

The above problems are avoided with an arrangement according to U.S. Pat. No. 4,493,691. In this arrangement, a TV camera is provided, which records the image visible through the transparent rotor of the separation chamber and reproduces it on a TV display. The adjustment of the position of the phase boundary is performed manually by a human operator.

Manual adjustment of the phase boundary based on visual observation of the phase boundaries entails significant disadvantages. The accuracy of the detection system is limited by the visual limitations of the human eye as well as the limitations of the TV technology itself. Furthermore, the presence of a trained person is essential during the entire operation of the separation device. This conventional method is thus less than optimal and can be performed only with high technical and personnel expenditure.

The object of the invention is, starting from the device mentioned in the introduction, to refine it with a phase detector which automatically detects and adjusts the phase boundary such that it has differentiated detection capability and adjustment behavior and thus increases the potentials for use of the separation device along with greatly improved separation performance.

SUMMARY OF THE INVENTION

In accordance with the present invention, there is provided a device for separation of media into its components wherein the light source and the light receiving arrangement with optics are disposed such that the light receiving arrangement receives light signals corresponding to the brightness values of the light reflected from the components and the control circuit is designed such that control signals can be triggered based on the differences in brightness.

Consequently, with the device according to the invention, the distinction is not made, as in the known case of the EP patent, merely between dark and light components of the medium through a group of punched holes, but is instead made between components with differing degrees of brightness.

The phase detector according to the invention is thus capable of differentiating between the different levels of brightness or coloration of the fractions or components to be separated and capable of performing the adjustment of operational parameters based on that. In this manner the radial position of the phase boundary can be specified differentiably in the separation chamber. Thus it is possible with the present invention to detect the phase boundaries significantly more accurately than is possible with prior art phase detectors. It is also possible to differentiably detect individual components separated from each other during centrifugation. An application in the area, for example, of blood cell separation thus enables differentiation as well as determination of the radial thickness of the layers of red and white blood cells, sedimented thrombocytes, and blood plasma. Furthermore, it is possible to determine the thrombocyte content of the blood plasma based on the changes in brightness of the blood plasma.

In addition, the separation device with the phase detector according to the invention can also be used with turbid media which are thus impermeable to light. This opens up new possibilities for treatment even in the clinical area.

BRIEF DESCRIPTION OF THE DRAWINGS

The invention may be better understood with reference to the accompanying drawings, in which.

DETAILED DESCRIPTION OF THE INVENTION

Figure 1:
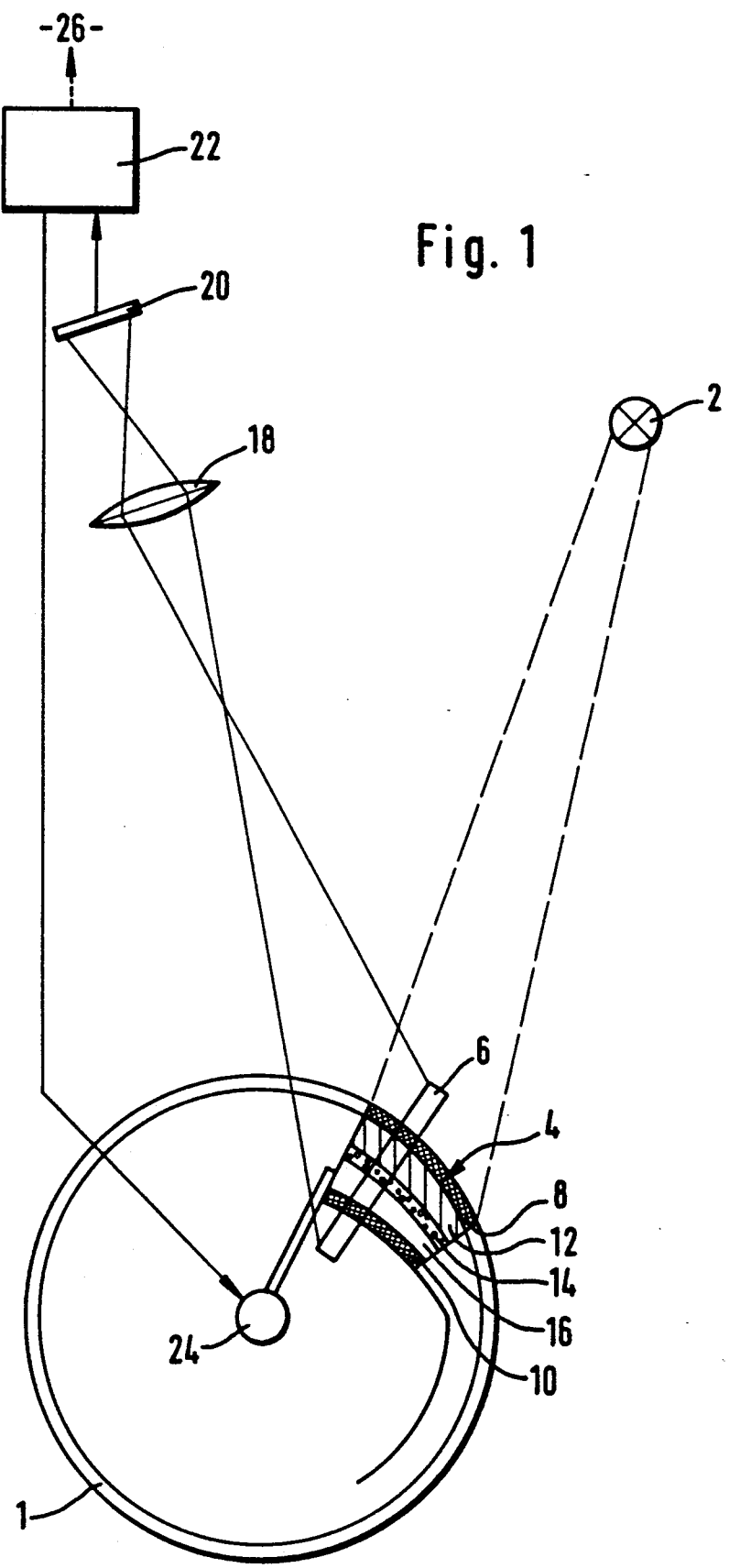
FIG. 1 illustrates an arrangement for detection and adjustment of the phase boundary between the fractions in a blood centrifuge (phase detector) presented schematically.

The present invention is superior to the conventional method of visual phase boundary observation and manual adjustment both because of the precision of the detection unit and because of the rapid and certain processing in the electrical circuit of a calculation and adjustment unit.

According to an embodiment of the invention, the device is refined such that the light receiving arrangement comprises an arrangement of at least two photosensors separated from each other, which deliver output signals selectively and proportionally to the brightness of the components to be separated, to which output signals a computing unit is connected downstream as a control circuit, whereby the computing unit, preferably a microprocessor, processes the output signals and controls at least one downstream stage according to a program which may be entered in advance.

With such a light receiving arrangement and control circuit, particularly advantageous detection and adjustment of the phase boundary are possible. The photosensors of this light receiving arrangement are appropriately disposed in a linear pattern and preferably form a so-called CCD line sensor. Such a receiving arrangement and computing unit operates very quickly and accurately, such that optimum separation performance of the separation device is assured via the downstream stage.

The downstream stage can be an adjustment element (regulation unit) for the control of the phase boundary, preferably a pump for removal of a separated fraction. In the case of blood separation, this pump is preferably a plasma pump. By changing the plasma flow, the position of the phase boundary can be changed or the thickness of the layers of the individual fractions in the chamber can be adjusted. However, the downstream stage can even be a printer or a plotter or a display, whereby the downstream stages can also be provided in combination.

According to an advantageous embodiment of the device, the light source is disposed such that it illuminates the specified region of the separation chamber directly or the light receiving arrangement is disposed with the optics such that reflected light can be reproduced on the light receiving arrangement. With such a beam path, the brightness differences in the components are particularly clearly representable.

In principle, it is also conceivable to use a light source which, depending on the medium to be separated, causes its components to fluoresce differently. The brightnesses are expressed in this case through different intensities of fluorescence.

According to an embodiment of the invention, the light source can be switched on intermittently, preferably in synchronization with the rotation of the separation chamber. This can occur, for example, with the use of a stroboscope. It is also conceivable to trigger the activation of the light source using various stimuli. Triggering based on the rotation speed or depending on the angular position of the rotor of the separation chamber or by an optical and/or magnetic or electrical marking is conceivable. Generally speaking, the light source can therefore be triggered by a marking on a disposable element or by the geometry of the drive mechanism of the separation chamber.

Temporal modification of the moment which triggers the light provides an additional possible preferred application. With this it is possible to scan different regions of the separation chamber and thus, for example, to generate a two-dimensional image or a plurality of one-dimensional images in completely different regions of the chamber. Turbulent movements in the separation chamber are thus readily detectable.

According to another embodiment of the invention, an infrared light diode is provided as the light source. These light diodes generate brief flashes of light which can be particularly simply triggered by the above-mentioned control signals. Furthermore, a very efficient illumination system is provided through the use of infrared light diodes. Preferably the diodes are disposed in the form of a circle around a lens such that their maximum intensity of illumination is concentrated on the specified scanning field. The reflected light is directed to appropriate photosensors by special optics.

It is particularly advantageous if the separation chamber has a transparent radial window in the specific region illuminated by the light source. This window is advantageously bounded on its outer and inner regions respectively by a reference stripe, whereby both reference stripes have a constant, known brightness value. Thus, it is possible to avoid effects of tolerances and temperature drifts of components or the fouling of the optics; it can be used for adjustment of the electrical circuit. The reference stripes can at the same time be used for detection of the edge of the separation chamber. Additionally, the application of the reference stripes permits detection of mechanical displacements of the separation chamber within specific limits, with the possibility of correction of said displacements in the electrical circuit. In additon to the detection of the phase boundaries, the arrangement can be disposed such that the light receiving arrangement receives light signals corresponding to the absorption in components by translumination for measurement of hemolysis.

Additional design characteristics, advantages, and possible applications of the invention are revealed through one exemplary embodiment depicted in the drawings. FIG. 1 schematically depicts a separation chamber 1 of a blood centrifuge. Such blood centrifuges have become familiar in a variety of designs, for example, through the patents mentioned in the introduction. A schematic representation of the separation chamber of this blood centrifuge therefore suffices in the description of the phase detector according to the invention. The separation chamber 1 has a transparent radial window 4 in a specific region illuminated by a light source 2. The phase boundaries are observable in this region, the scanning field. The scanning field 4 is bounded on its outer and inner regions respectively by a reference stripe 8 or 10. These two reference stripes have a constant, known brightness value. In the scanning field 4, three phases can be detected, i.e., an outer phase 12, the red blood cells (erythrocytes), a mixed phase 14 (the so-called buffy coat), and an inner plasma phase 16.

A radial section 6 of the scanning field 4 is transmitted via optics 18 to a light receiving arrangement 20, which is composed of photosensors arranged in a linear pattern, a so-called line sensor. The output signals of this light receiving arrangement, which are an electrical image of the differences in brightness between the individual fractions, are transmitted to a computing unit 22, which is preferably a microprocessor. This computing unit controls downstream stages according to a preestablished program, for example, an adjustment element 24 for changing the position of the phase boundary. In a blood centrifuge, this adjustment element consists preferably of a plasma pump which removes the plasma fraction from the separation chamber. The downstream stage can also be, for example, a display 26 on which the information is displayed graphically.

The light source 2 intermittently illuminates the specified scanning field 4 in synchronization with the speed of the separation chamber. In a preferred embodiment, the illumination occurs via light diodes in the infrared range. The light diodes generate brief flashes of light which can be triggered by various control signals. Triggering by the rotation speed or the angular position of the rotor of the separation chamber or by an optical or magnetic or electrical marking is also conceivable. Furthermore, it is possible to provide a very efficient illumination system using infrared light diodes. Preferably the diodes are disposed in the form of a circle around a lens such that their maximum intensity of illumination is concentrated on the specified scanning field 4. In principle, illumination using a stroboscope is also possible.

Because of their known, constant brightness values, the reference stripes 8 and 10 can be used for adjustment of stages 22 and 24. Thus effects of tolerances and temperature drifts of components or fouling of the optics can be avoided. Furthermore, the reference stripes enable the detection of mechanical displacements of the separation chamber within specific limits, whereby said displacements can be corrected by stages 22 or 24.

Figure 2:
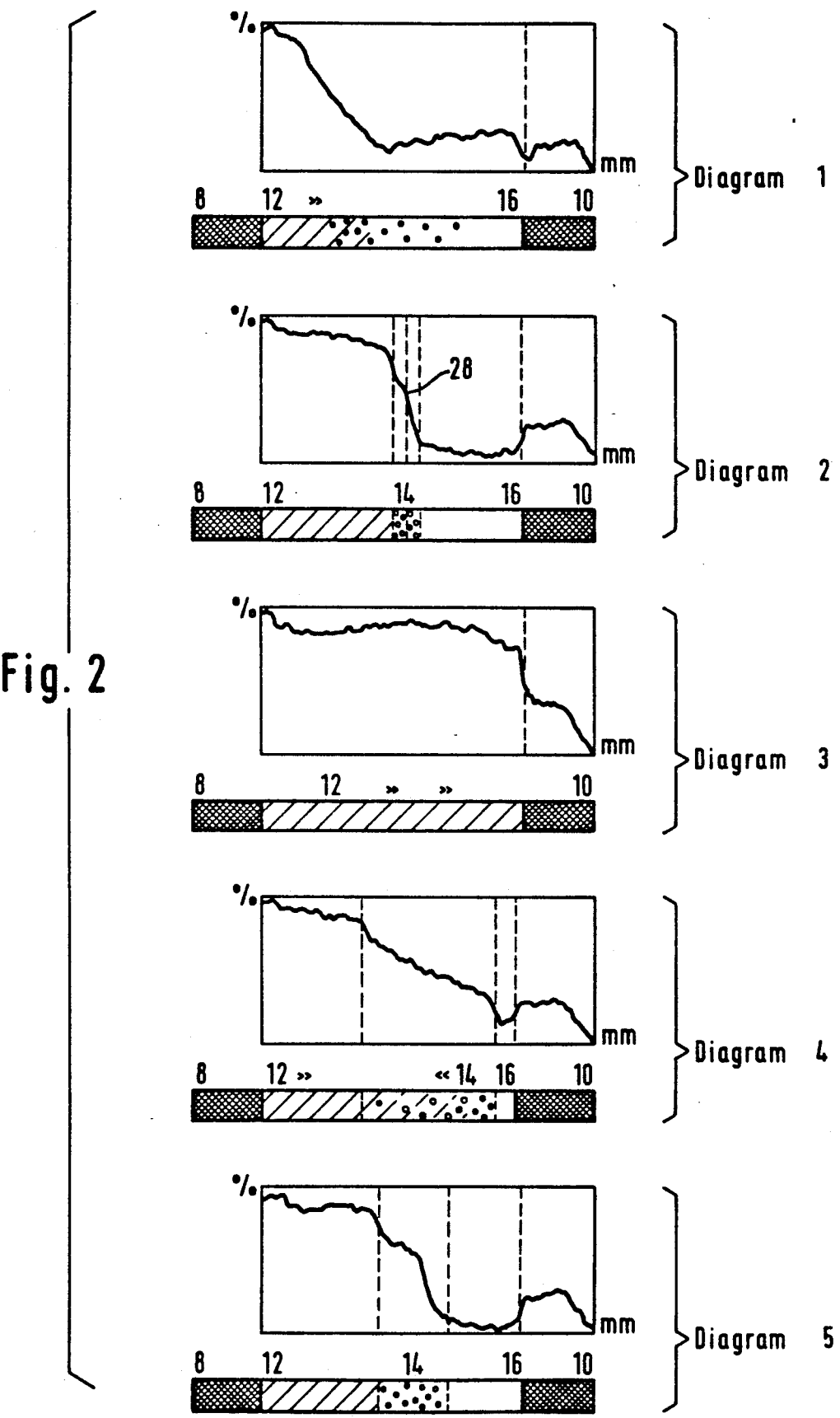
FIGS. 2A–2E comprise five diagrams depicting the phase boundary under differing conditions.

To illustrate the accuracy of the signals received by the light receiving arrangement and processed in the computing unit 22, five diagrams are shown in FIG. 2, whose ordinates represent the light intensity, i.e., the brightness, and whose abscissae represent the radial window 6 in the scanning field 4. The schematic representation of the radial section is in each case presented below the associated diagram. The numbering of the individual sections of the radial window corresponds to the reference numbers in FIG. 1 in the scanning field 4.

The first diagram depicts the graphic image of a phase boundary in the process of formation. On the outer edge, already concentrated red blood cells 12 appear, with a transition without a defined boundary to a clear plasma phase 16. Diagram 2 shows the graphic representation of a separation with a stable phase boundary. A thin mixed phase 14 sediments between the red blood cells 12 and the plasma 16. Generally, thrombocytes 28, which are difficult to detect and consequently to extract, are also found in this fraction. The accuracy of the phase detector according to the invention based on the differences in brightness of the components of the blood is demonstrated here in the detection of these cells, which can be seen in the diagram as unevenness in the otherwise straight phase boundary line.

With the use of the regulating unit 24, a plasma pump in the present case, the phase boundary can be shifted. This can occur manually or can be controlled according to the invention via the computing unit 22 according to a program.

To extract some separated blood components, the plasma pump is activated until a phase boundary can no longer be detected and only red blood cells are found in the separation chamber. The signals received at this time by the line sensor 20 are depicted in Diagram 3. The signals are processed by the computing unit 22 and the plasma pump is stopped accordingly. After addition of new blood, a new phase boundary can form after initial turbulence. The signals received by the sensor during the turbulence are shown in Diagram 4, with a subsequently stabilizing phase boundary in Diagram 5.

It is particularly clear from the diagrams in FIG. 2 what differentiated detection capability the phase detector according to the invention has based on the detection of the differences in brightness of the components and what differentiated control processes can be triggered with it.

Figure 3:
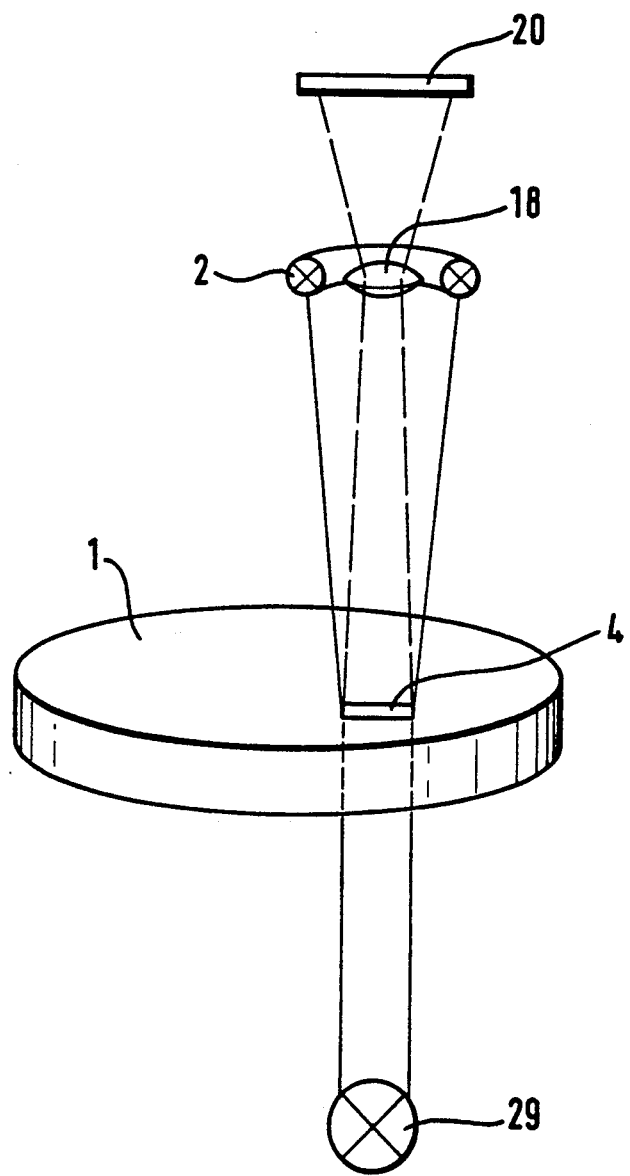
FIG. 3 depicts an arrangement according to FIG. 1 with additional means for measurement of hemolysis.

FIG. 3 depicts an additional exemplary embodiment of the invention in which in addition to the detection of the phase boundary in blood separation using the brightness values of the reflected light, as described using FIGS. 1 and 2, hemolysis is measured by the absorption of translumination. The degree of hemolysis is determined from the degree of absorption of the blood plasma.

FIG. 3 depicts in a schematic elevation first the arrangement according to FIG. 1. Elements corresponding to this arrangement are provided with the same reference numbers. The light sources 2 disposed in the form of a circle illuminate the scanning field 4 of the separation chamber 1 in direct illumination, while the photoelectric receiver, preferably the line sensor 20, receives the brightness value of the reflected light via the optics 18.

In addition, a light source 29 is provided which illuminates the scanning field 4 in the opposite direction from the light sources 2 with translumination. The light passing through the fractionated components is likewise directed by the optics 18 to the receiver 20. The light source 29 can, in a first embodiment, also be pulsed alternatingly like the light source 2 and, in a second embodiment, can illuminate the scanning field 4 simultaneously with the light source 2.

The resolution of the transparent phase, i.e., of the plasma, is improved with the use of the translumination generated by the light source 29. With the increased degree of brightness, an improved contrast compared to the dark region, e.g., the RBC region, can thus be generated. For one thing, with the improved resolution in the bright region, the transition from the dark to the bright region is improved, resulting in better determination of the hairline boundary between RBC and plasma. Furthermore, the gradations in the bright region are more readily detectable. Thus, the brightest region, represented by unaffected plasma, can be more readily differentiated from somewhat turbid plasma and this in turn from plasma which is colored red because of hemolysis. Thus, the resolution is improved overall by this.

As already mentioned, the light source 29 can be pulsed simultaneously or alternatingly with the light sources 2. In both cases, the detector advantageously undertakes an addition of the signals through the formation of integrals and thus determines the individual optical densities of the blood fractions as a function of the position of the scanning field 4.

What is claimed is:

1. A device for separation of media into their components through density centrifugation, comprising:
   a separation chamber;
   means for detection and adjustment of the phase boundary between at least two optically differentiable fractions of the medium;
   a light source which illuminates the separation chamber in a region of the phase boundaries which are adjusting themselves;
   a light receiving arrangement and optics which reproduce a specific section of the region on the light receiving arrangement, which responds to different light signals according to optical differences in the fractions; and
   an electrical control circuit means connected downstream from the light receiving arrangement to trigger control signals, wherein the light source and the light receiving arrangement are disposed with the optics such that the light receiving arrangement receives light signals corresponding to the brightness of the components and the control circuit is designed such that control signals can be triggered based on the differences in brightness.

2. The device according to claim 1, wherein the light receiving arrangement comprises an arrangement of at least two photosensors separate from each other, which deliver output signals selectively and proportionally to the brightness of the components to be separated, to which a computing unit means is connected downstream as a control circuit, whereby the computing unit means processes the output signals and controls at least one downstream stage according to a program which can be entered in advance.

3. The device according to claim 2, wherein the photosensors are disposed in a linear pattern.

4. The device according to claim 3, wherein the photosensors form a CCD line sensor.

5. The device according to claim 2, wherein the downstream stage is an adjustment element for the control of the phase boundary.

6. The device according to claim 5, wherein the downstream stage is a plasma pump for blood separation.

7. The device according to claim 2, wherein the downstream stage is a printer or a plotter.

8. The device according to claim 2, wherein the downstream stage is a display.

9. The device according to claim 1, wherein the light source is disposed such that it illuminates a specific region of the separation chamber with direct light and the light receiving arrangement is disposed such that the reflected light can be reproduced on the light receiving arrangement.

10. The device according to claim 9, wherein the light source can be switched on intermittently.

11. The device according to claim 10, wherein the light source is switched on in synchronization with the rotation of the separation chamber.

12. The device according to claim 10, wherein the light source is provided with at least one infrared light diode.

13. The device according to claim 1, wherein the separation chamber has a transparent radial window in the specific region illuminated by the light source.

14. The device according to claim 13, wherein the transparent radial window is bounded on its outer and inner regions respectively by a reference stripe and both reference stripes have a constant, known brightness value.

15. The device according to claim 1, wherein additional optical means are provided and disposed such that the separation chamber is transluminated in the region of the phase boundaries which are adjusting themselves opposite the illumination direction of the light source and the light receiving arrangement also receives light signals corresponding to the absorption in components by translumination.

* * * * *